US008960028B2

(12) United States Patent
Lambert et al.

(10) Patent No.: US 8,960,028 B2
(45) Date of Patent: Feb. 24, 2015

(54) METHOD FOR AUTOMATICALLY IDENTIFYING A MATERIAL OR AN OBJECT

(76) Inventors: Claude Lambert, Saint Michel sur Orge (FR); Jean-Michel Hachin, Levallois-Perret (FR)

( * ) Notice: Subject to any disclaimer, the term of this patent is extended or adjusted under 35 U.S.C. 154(b) by 138 days.

(21) Appl. No.: 13/058,096

(22) PCT Filed: Jul. 24, 2009

(86) PCT No.: PCT/FR2009/000926
§ 371 (c)(1), (2), (4) Date: Jun. 16, 2011

(87) PCT Pub. No.: WO2010/012892
PCT Pub. Date: Feb. 4, 2010

(65) Prior Publication Data

US 2011/0232398 A1 Sep. 29, 2011

(30) Foreign Application Priority Data

Jul. 30, 2008 (FR) ..................................... 08 04363
May 7, 2009 (FR) ..................................... 09 02217

(51) Int. Cl.
*G01N 33/00* (2006.01)
*B07C 5/342* (2006.01)

(52) U.S. Cl.
CPC .................................... *B07C 5/342* (2013.01)
USPC ........................................................ 73/866

(58) Field of Classification Search
None
See application file for complete search history.

(56) References Cited

U.S. PATENT DOCUMENTS 4,533,902 A * 8/1985 Baker et al. ........................ 341/9
4,733,760 A * 3/1988 Inagaki et al. ................ 477/185
2009/0200212 A1 8/2009 Hachin et al.

FOREIGN PATENT DOCUMENTS

FR 2901160 A1 11/2007
GB 2119509 A 11/1983
WO 9927623 A1 6/1999

OTHER PUBLICATIONS

International Search Report, dated Apr. 22, 2010, from corresponding PCT application.

* cited by examiner

*Primary Examiner* — Robert R Raevis
(74) *Attorney, Agent, or Firm* — Young & Thompson

(57) ABSTRACT

A method for identifying and/or authenticating a material or an object, especially for the purpose of sorting materials or objects, includes: an excitation step including application of excitation vectors to a material or an object; a detection step in which the responses of the materials or objects subjected to the excitation vectors are detected; and a step of determining at least one item of information relating to the material or object on the basis of the responses obtained and of a pre-established look-up table. These steps will have been preceded by the incorporation, into or on the surface of the materials or objects, of at least one substance selected so as to react to at least one excitation vector and by the generation of a look-up table consisting of a set of one-to-one relationships between a combination of responses and an item of information relating to the material.

24 Claims, 1 Drawing Sheet

METHOD FOR AUTOMATICALLY IDENTIFYING A MATERIAL OR AN OBJECT

BACKGROUND OF THE INVENTION

1. Field of the Invention

The present invention relates to a method for automatic identification of objects or materials, for example plastic materials. By identification, is meant the extraction of information relating to the material or to the object.

This method is notably applicable to the sorting and recycling of materials originating from used objects.

2. Description of the Related Art

Methods for automatic identification of objects or materials are known, consisting of including in these objects or materials small concentrations of substances having specific luminescent properties, of irradiating them with a light beam with a wide frequency spectrum, of carrying out a spectrophotometric analysis of the response of the substances included in the material and of identifying them depending on these responses.

In their application No. 06 04578, the Applicants have for example proposed a method in which the spectrophotometric analysis notably includes the following steps, after irradiation of the object or of the marked material:

- sending the waves transmitted or reflected by the object or the material onto a dispersing element which deflects them so as to obtain a light spectrum of the light intensity at different zones of the spectrum corresponding to different wavelength ranges,
- detecting the light intensity in each of said zones,
- comparing this intensity with one or more threshold values specifically allocated to this zone and which have been stored in memory beforehand,
- the result of this comparison contributing towards determining the identity code of the material.

However, this method is intrinsically limited in the capacity of coding information relating to the material because of the unicity of this type of excitation. Now, it may be useful to code several types of information relating to a material, for example its composition, its recycling route, its manufacturer.

It is also limited in the case of strongly colored or black materials which are relatively frequent. Coloration is due to the presence within the material of colored pigments, notably carbon black, in variable proportions. Carbon black is used as a protective agent against radiations, mainly UV radiation, in outdoor applications or as a stabilizing and strengthening agent. Its action mainly consists of absorbing the radiations received by the material which may cause degradations of the polymeric chains. However, it also has the property of absorbing radiations which may be notably emitted in the visible spectrum by the material making up the object and/or the included markers, which explains its dark or black color. The result of this is that excitation by a light source does not cause any spectral emission allowing easy extraction of information relating to the material with very small concentrations of markers if the latter is strongly colored or black.

BRIEF SUMMARY OF THE INVENTION

More particularly, the object of the invention is therefore to solve this problem by means of a method with which different materials with very small concentrations of markers may be identified independently of their color.

According to the invention, this method comprises the following steps:

- an excitation step including the application to a material or to an object of a plurality of excitation vectors,
- a step for detecting the responses of the materials or objects subject to said excitation vectors,
- a step for determining at least one piece of information relating to said material or to said object on the basis of matching said obtained responses and a pre-established correspondence table.

The method consists of subjecting a material or an object to a combination of different excitation vectors and no longer only to a light excitation. The excitation vectors may be applied either simultaneously or sequentially.

Advantageously, the method may be preceded by a phase including:

- a step for selecting at least one substance reacting to at least one of said excitation vectors by emitting a remotely detectable response, said substances being provided in order to be incorporated within or at the surface of materials without substantially modifying the physical or chemical properties of said materials,
- a step for elaborating a correspondence table consisting in a set of one-to-one relationships between a combination of responses and information relating to said material, and a marking step in which at least one substance selected within or at the surface of the material is selectively incorporated, in order to activate said material or objects consisting of said material.

In this preliminary phase, at least one substance is selected which may be incorporated into materials, for example plastic materials, at a very low concentration, each substance $S_i$ having a response $R_{i,j}$ to an excitation vector $V_j$. Each substance does not have to respond to each excitation vector, it is sufficient that it responds to at least one excitation vector.

In the most current case, a substance $S_i$ responds to the excitation vector $V_i$ and there are as many substances as there are excitation vectors. However two substances may respond to the same excitation vector provided that their responses are distinct, for example in fluorescence, at different wavelengths. The number of substances used in a material may therefore be larger than the number of excitation vectors. Conversely, the number of substances may be less than the number of excitation vectors in the case when one or more substances would respond to different excitation vectors. Multiplication of the excitation vectors has the benefit of allowing resorting to wider families of substances and therefore broadening the coding.

The very small concentration used for the substances is essential:

- it guarantees that incorporation of the substances will not modify the physical or chemical properties of the materials into which they will be incorporated,
- non-toxicity tests are omitted,
- the substances used will be detectable with difficulty and notably invisible to the naked eye,
- additional expenditure will be low.

The substances may be of different nature:

- chemical compounds,
- particles, notably nanoparticles, i.e. particles or structures, the size of which is measured in nanometers.

The substances may be embedded into the bulk or positioned at the surface, for example by impregnation (for example in a textile, a tincture . . . ), by coating (varnish, paint coating, spraying) on various supports, for example aircraft metal parts, whether this be on the whole of the surface or punctually (screen-printing, brush plating) or as marked labels either partly visible or not.

Advantageously, this coating may comprise a reflecting area covered with a transparent layer containing markers. With this technique, it is thereby possible to carry out spectrophotometry by reflection which considerably reduces the energy losses.

As the responses of the substances to the different excitation vectors are known, it is possible to elaborate a correspondence table between combinations of substances and therefore responses to excitations and information provided for the materials in which they will be incorporated. For example, if three substances $S_1$, $S_2$ and $S_3$ and two excitation vectors $V_1$ and $V_2$ are used and if:

- substance $S_1$ provides a response $R_{1,1}$ to the excitation $V_1$,
- substance $S_2$ provides a response $R_{2,1}$ to the excitation $V_1$,
- substance $S_3$ provides a response $R_{3,2}$ to the excitation $V_2$, $2^3-1=7$ combinations of possible responses are obtained, and therefore a correspondence table with 7 inputs.

More generally, the use of n marking substances in a material ($n \geq 1$), subject to p excitation vectors ($p \geq 2$), in order to obtain r responses ($r \leq n*p$) enables a correspondence table to be constructed with $2^r-1$ inputs, and therefore to be coded with as many pieces of information relating to the material.

This may therefore result in a great possibility of coding information relating to a material or to an object incorporating these materials by multiplying the excitation vectors and the substances.

In the step for determining information relating to said material or to said object:

- said obtained responses are compared to combinations of responses present in said correspondence table,
- said information is allocated when said comparison reveals an identity.

The excitations to which the material is subject cause one or more responses. These responses are matched with the correspondence table between expected responses and information concerning the material, which for example enables identification of this material. If no response is obtained, or if the obtained response does not appear in the correspondence table, it will not be possible to allocate information concerning the material.

In a step for elaborating the correspondence table, it is possible to only take into account the presence or the absence of a substance response to the excitation vectors, and/or the intensity of a substance response, for example as a plurality of response thresholds.

The spontaneous emission of a selected substance in the absence of any excitation vector may also be taken into account, for example in the form of spontaneous emission of electromagnetic radiation or particles, either neutral or charged particles, notably in the case of radioactivity, or of emission of molecules, notably odorous molecules.

Advantageously, in the detection step, it is possible to take into account the emission of the material under the effect of the excitation vectors, notably for correcting the obtained responses, for example for subtracting background noise.

A large number of excitation vectors may be contemplated:

- an electromagnetic excitation, notably an optical excitation, for example a light beam with a wide frequency spectrum in the infrared or UV, X rays,
- an electrical excitation, for example as the application of an electric field,
- a magnetic excitation, for example as the application of a magnetic field,
- a thermal excitation,
- an excitation by a particle flux, notably of electrons.

Advantageously, the provided responses from the substances and the obtained responses are selected from the list including:

- electromagnetic emission, notably light emission, fluorescence (visible, X, UV) or phosphorescence,
- magnetic field variation,
- electric field variation.

As indicated above, these responses are remotely detectable.

Advantageously:

- in the marking step, the materials or objects are marked with a marker including yttrium vanadate doped with europium, at a concentration of less than 200 ppm, or even less than 100 ppm,
- in the excitation step, an electromagnetic excitation in the range comprised between 230 and 390 nm, preferentially 330-340 nm is applied to the material or the object,
- in the detection step, detection of said marker within a band centered on 610-620 nm and measurement of the intensity of the corresponding peak are carried out.

Yttrium vanadate doped with europium, excited between 230 and 390 nm, i.e. in the near UV, used alone or in combination with other markers, provides a response centered on 610-620 nm which may exploited in black or strongly colored materials.

When a black or strongly colored material is excited in the near UV, a relatively large background noise is observed, which requires signal processing, for example in order to form a baseline, so as to extract and quantify the responses. When yttrium vanadate doped with europium is used in combination with another marker, one of them may be used as a calibration, one then operates differentially.

With the method, it is possible to collect one or more pieces of information relating to a material or an object, for example a chemical property, notably its chemical composition and therefore identify the material being examined or its quality (type, grade). The information may also relate to the manufacturing of the material or of the object, for example the identity of its manufacturer, its location or its manufacturing date . . . .

Thus, a transition is performed from simple identification of a material or of an object to its authentication, i.e. the possibility of distinguishing an authentic object from a non-authorized copy, for example within the scope of the struggle against counterfeiting.

By its generality, the method is applicable to any types of materials, notably black or strongly colored materials, which absorb a large range of radiations.

In the case of an excitation by a light beam, the identification data may include the combination of selected markers, the wavelength of the characteristic radiation lines, their intensity, the duration of possible fluorescence . . . .

Thus, it is unnecessary to observe all the wavelengths emitted by the material, it is sufficient to analyze the ranges of values corresponding to the lines provided in the correspondence table, stored in memory beforehand, in order to check their presence or their absence without being concerned with the zones located outside these lines.

The identification code may result from a combination of markers and may consist in a binary number, the binary figures of which each correspond to the presence or the absence of a marker.

In the case of an identification with view to recycling materials, the use of this combination of markers may be contemplated in order to code the type or the grade of materials, for example plastic materials, which enables them to be sorted per type or per grade once identification is achieved. The code may also relate:

to the beneficiation, recycling, rejection or elimination route, this route may be common for materials of different compositions and may change over time, to the fact of being aware that the material has a particular property, for example if it is a secondary i.e. already recycled raw material.

By extension, by combining several excitation vectors and markers it is possible to obtain several pieces of information of different nature on a material, for example the authentication of one or more actors during the life cycle of a material or of an object (manufacturer, distributor, owner . . . ); for this purpose, it is sufficient that the material incorporated into the object has been marked beforehand depending on one or more actors involved in the life cycle of a material or of an object and not only on its composition.

The method is therefore applicable:

- to the sorting of materials or objects,
- to the recycling of materials or objects,
- to the traceability of materials or objects,
- to quality control, for example checking whether a batch of already sorted materials actually corresponds to the announced composition, in order to optimize the recycling operations.

The method is applied to the identification of any type of material, notably materials with any more or less dark coloration; it is particularly applicable to the identification of colored or black materials.

BRIEF DESCRIPTION OF THE DRAWINGS

Examples of markers suitable for novel plastic materials will be described hereafter as non-limiting examples with reference to the appended drawings wherein.

DETAILED DESCRIPTION OF THE PREFERRED EMBODIMENTS

Figure 1:
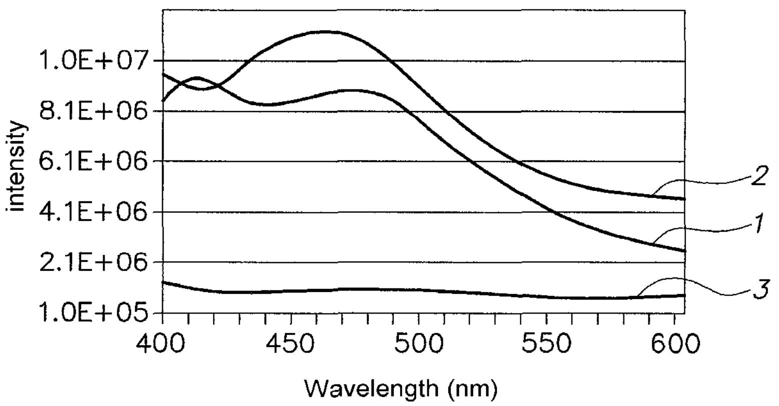
FIG. 1 illustrates natural fluorescence curves of three plastic compounds.

FIG. 1 illustrates the fluorescence intensity curves of three non-marked plastic compounds, acrylonitrile-butadiene-styrene (ABS, curve 1), polypropylene (PP, curve 2) and black-pigmented polypropylene (curve 3), ABS and PP being two materials currently used. The illumination is produced by means of a UV-TOP light-emitting diode (LED) operating at about 330 nm, i.e. in the near UV, with a rated output power of 1 mW and the spectra are obtained with a fluorescent spectrometer FluoroMax®.

It is seen:

- that the natural fluorescent intensity of ABS and of PP decreases in the region of the red and near infrared ($\lambda$>500 nm),
- that the fluorescence intensity of black-pigmented PP is constant in the whole visible and near IR domain, but with a lower intensity by more than two orders of magnitude than that of non-pigmented samples.

Taking into account the lower intrinsic response of these materials in the red and near IR domain on the one hand and the uniformly low response of the black-pigmented material, it is inferred therefrom that it may be advantageous to use markers which, after irradiation of the marked object or material, emit radiations in a frequency band corresponding to red—near infrared.

Advantageously, markers will be selected which have a response in the range from 500 to 650 nm.

Taking into account the Stokes shift, the irradiation should take place in a range of smaller wavelengths, for example in the near UV, in the 220-380 nm range.

The markers used may be chemical, organic or mineral, or consist of nanoparticles. These may be products made on demand or commercial products. For example, markers marketed by "Phosphor Technology Dyes" (registered trade name) may be used, the characteristics of which are the following:

- marker H: two emission peaks at 614 and 618 nm,
- marker I: an emission peak at 515 nm.

These markers further have the advantage of exhibiting good thermal and chemical stability, as well as good UV-fastness.

In order to obtain signals with which the material will be identified:

- a high power excitation source will be used, typically a Xenon arc lamp, a UV LED or a laser;
- it will be proceeded with amplification of the signal corresponding to said transmitted or reflected light intensities;
- signal processing corresponding to said emitted radiations will be carried out in order to reduce the background noise, in particular by exploiting the level of the characteristic peaks of the marker(s).

Figure 2:
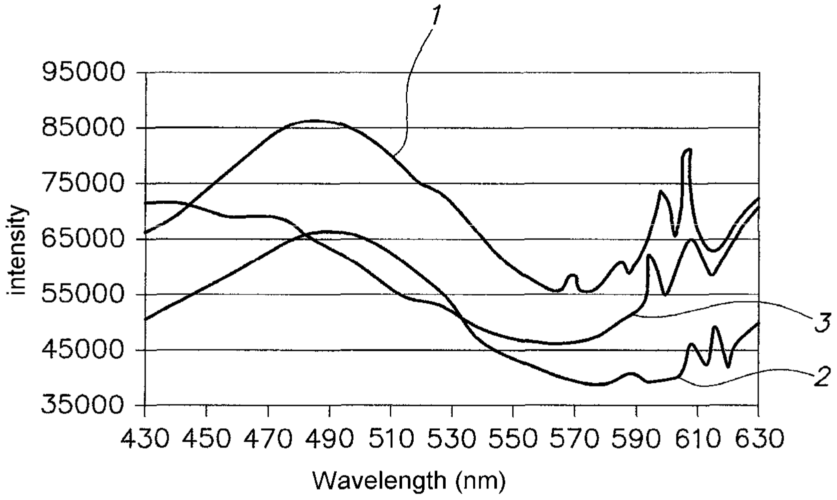
FIG. 2 illustrates fluorescence curves of black polypropylyne, with different marker concentrations.

FIG. 2 illustrates the results obtained on the Xenon arc lamp and a fluorescence spectrometer FluoroMax®, in the case of black polypropylene marked with the marker H, at two different concentrations, 200 ppm (curve 1) and 100 ppm (curves 2 and 3). It is seen that the two characteristic peaks of the marker H clearly emerge from the background noise at 614 and 618 nm, thereby allowing its identification and thereby actual identification of the material in which it is included, even when it is black.

The invention claimed is:

1. A method for identifying and/or authenticating a material or an object, the method comprising:

- selecting at least one substance configured to react to at least one excitation energy by emitting a remotely detectable response, the at least one substance being provided in order to be incorporated within or at a surface of the material or the object without substantially modifying physical or chemical properties of the material or the object;
- establishing a correspondence table consisting in a set of one-to-one relationships between a combination of responses and pieces of information concerning the material;
- selectively incorporating the at least one selected substance within or at the surface of the material to identify the material, to activate the material or objects consisting of the material;
- applying at least one excitation energy to the material or to the object by an excitation source outputting the at least one excitation energy to be conveyed to the material or the object;
- detecting one or more responses of the material or object subject to the excitation energy;
- determining at least one piece of information about one or more of a physical property of the material or the object and an identification detail of the material or the object based on the one or more obtained responses and a pre-established correspondence table; and
- identifying and/or authenticating the material or the object based on the determined piece of information, wherein the selecting, the establishing, and the selectively incorporating occur before the applying, the detecting, and the determining.

2. The method according to claim 1, wherein the determining the piece of information concerning said material or said object comprises:

comparing the obtained responses with the combinations of responses present in the correspondence table, and allocating the information when the comparison reveals an identity of the material.

3. The method according to claim 1, wherein, in the establishing the correspondence table, a presence or an absence of a substance response to the at least one excitation energy is only taken into account.

4. The method according to claim 1, wherein, in the establishing the correspondence table, an intensity of a substance response to the at least one excitation energy is taken into account.

5. The method according to claim 1, wherein, in the establishing the correspondence table, a spontaneous emission of a selected substance is taken into account.

6. The method according to claim 5, wherein the spontaneous emission is selected from the list including:

an emission of electromagnetic radiation, an emission of either neutral or charged particles, and an emission of molecules.

7. The method according to claim 1, wherein, in the detecting the one or more responses, a response of the material under an effect of the at least one excitation energy is taken into account to correct the one or more obtained responses.

8. The method according to claim 1, wherein the at least one excitation energy is selected from a list including:

an electromagnetic excitation, the electromagnetic excitation being an optical excitation, an electrical excitation, a magnetic excitation, a thermal excitation, and an excitation by a flow of particles, the particles being electrons.

9. The method according to claim 8, wherein the one or more responses are selected from the list including:

an electromagnetic emission, the electromagnetic emission being an optical emission, a magnetic field variation, and an electric field variation.

10. The method according to claim 9, wherein an identification material including yttrium vanadate doped with europium, at a concentration of less than 200 ppm, is added to the materials or objects in the excitation application, an electromagnetic excitation in a range comprised between 230 and 390 nm is applied to the material or the object, and in the detecting, the identification material is detected in a band centered on 610-620 nm and measuring an intensity of the corresponding peak.

11. The method according to claim 10, wherein the yttrium vanadate is doped with the europium at a concentration of less than 100 ppm.

12. The method according to claim 1, wherein the information about the material is a chemical property, the chemical property being a chemical composition of the material.

13. The method according to claim 1, wherein the information about the material concerns manufacturing of the material.

14. The method according to claim 1, wherein the material is black or strongly colored.

15. The method according to claim 1, wherein the incorporated substance is a chemical which, after irradiation of the object or material, emits radiation in a band of frequencies corresponding to red-near infrared.

16. The method according to claim 15, wherein the incorporated substance emits radiations in a range from 500 to 650 nm.

17. The method according to claim 15, wherein the irradiation of the object or of the incorporated substance is carried out in a range from 220 to 380 nm.

18. The method according to claim 15, further comprising performing spectrophotometric analysis on the radiation including:

amplifying a signal corresponding to transmitted or reflected light intensities, and processing the signal corresponding to the emitted radiations to reduce background noise.

19. The method according to claim 1, further comprising, prior to the excitation application, milling objects as particles, the at least one excitation energy being applied to the particles.

20. A method, comprising:

sorting materials or objects according to the method for identifying and/or authenticating a material or an object of claim 1.

21. A method, comprising:

recycling materials or objects according to the method for identifying and/or authenticating a material or an object of claim 1.

22. A method, comprising:

authenticating at least one of a manufacturer, a distributor, and an owner of a material or of an object in a life cycle of the material or of the object by applying at least one excitation energy to the material or to the object by an excitation source outputting the at least one excitation energy to be conveyed to the material or the object, detecting one or more responses of the material or object subject to the excitation energy, determining at least one piece of information about one or more of a physical property of the material or the object and an identification detail of the material or the object based on the one or more obtained responses and a pre-established correspondence table, and identifying and/or authenticating the material or the object based on the determined piece of information.

23. A method, comprising:

identifying materials or objects according to the method for identifying and/or authenticating a material or an object of claim 1.

24. A method, comprising:

performing quality control of materials or objects according to the method for identifying and/or authenticating a material or an object of claim 1.

* * * * *